(12) United States Patent  (10) Patent No.: US 9,168,244 B2
Pfarr et al.  (45) Date of Patent:  Oct. 27, 2015

(54) COMPOUNDS FOR USE IN THE TREATMENT OF FILARIASIS

(71) Applicant: RHEINISCHE FRIEDRICH-WILHELMS UNIVERSITAET BONN, Bonn (DE)

(72) Inventors: Kenneth Michael Pfarr, Bonn (DE); Achim Hoerauf, Bonn (DE); Gabriele Maria Koenig, Bonn (DE); Sabine Specht, Bonn (DE); Andrea Schiefer, Koenigswinter (DE); Till Friedrich Schaeberle, Bonn (DE); Alexander Schmitz, Andernach (DE); Stefan Kehraus, Alfter (DE)

(73) Assignee: RHEINISCHE FRIEDRICH-WILHELMS UNIVERSITAET BONN, Bonn (DE)

( * ) Notice: Subject to any disclaimer, the term of this patent is extended or adjusted under 35 U.S.C. 154(b) by 0 days.

(21) Appl. No.: 14/658,271

(22) Filed: Mar. 16, 2015

(65) Prior Publication Data
US 2015/0182497 A1   Jul. 2, 2015

Related U.S. Application Data

(62) Division of application No. 14/115,358, filed as application No. PCT/EP2012/058256 on May 4, 2012, now abandoned.

(30) Foreign Application Priority Data

May 5, 2011   (EP) .................................. 11164963

(51) Int. Cl.
  *A01N 43/16*   (2006.01)
  *A61K 31/35*   (2006.01)
  *A61K 31/366*   (2006.01)
  *C07D 309/38*   (2006.01)

(52) U.S. Cl.
  CPC ............ *A61K 31/366* (2013.01); *C07D 309/38* (2013.01)

(58) Field of Classification Search
  None
  See application file for complete search history.

(56) References Cited

FOREIGN PATENT DOCUMENTS

DE    3305974 A1 *  8/1984

OTHER PUBLICATIONS

Taylor et al. (Current opinion in infectious disease, 2001, 14, 727-731).*

*Primary Examiner* — Anna Pagonakis
*Assistant Examiner* — Daniel M Podgorski
(74) *Attorney, Agent, or Firm* — Norman B. Thot

(57) ABSTRACT

A method for a therapeutic treatment of filariasis includes administering to a subject in need thereof an effective amount of a compound of the general formula (1)

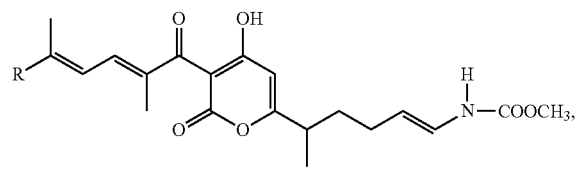

or at least one of racemates, enantiomers, diastereomers, solvates, hydrates, pharmaceutically acceptable salts, and esters of general formula (1), wherein,
  R is selected from the group comprising n-propyl, n-butyl, and at least one of structural elements (2a), (2b), (3a), (3b), (4), (5), (6a), (6b), (7a), and (7b):

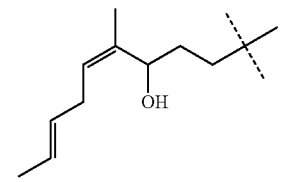

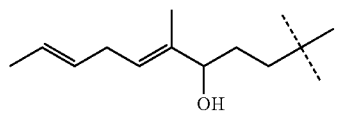

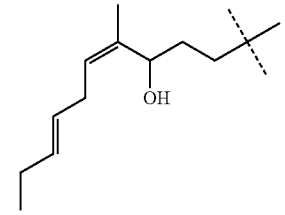

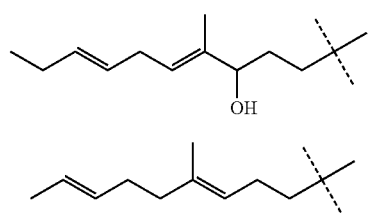

-continued
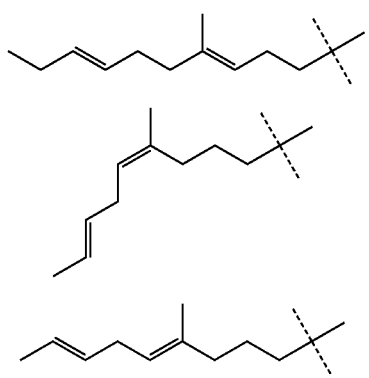
(5)
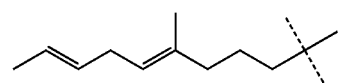
(6a)
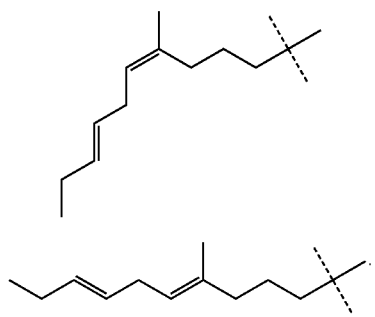
(7a)
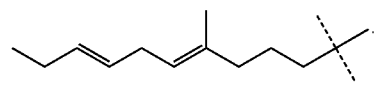
(7b)
(6b)
12 Claims, No Drawings

COMPOUNDS FOR USE IN THE TREATMENT OF FILARIASIS

CROSS REFERENCE TO PRIOR APPLICATIONS

This application is a divisional of U.S. application Ser. No. 14/115,358, filed on Nov. 4, 2013. U.S. application Ser. No. 14/115,358 is a U.S. National Phase application under 35 U.S.C. §371 of International Application No. PCT/EP2012/058256, filed on May 4, 2012 and which claims benefit to European Patent Application No. 11164963.8, filed on May 5, 2011. The International Application was published in English on Nov. 8, 2012 as WO 2012/150340 A1 under PCT Article 21(2).

FIELD

The present invention relates to compounds for use in the treatment of filariasis, pharmaceutical compositions, and methods for treating filariasis.

BACKGROUND

Filariasis is a parasitic disease that is caused by thread-like filarial nematodes or roundworms. Filariasis is a vector-borne disease that is transmitted via insect bites. Infective larvae of the nematodes can be introduced into the human body via bites of blood sucking insects such as mosquitoes or flies.

Filariasis can also affect domestic animals such as dogs. In dogs, dirofilariasis which is also called heartworm disease, is caused by nematodes called *Dirofilaria immitis* and *Dirofilaria repens*. Dirofilariasis is considered endemic in 49 States of the United States. The vectors are also blood sucking insects such as mosquitoes.

The major causes of human filariasis are the filarial nematodes *Wuchereria bancrofti*, *Brugia malayi*, *Brugia timori*, *Onchocerca volvulus* and *Mansonella* species that have human hosts. The nematodes *Wuchereria bancrofti*, *Brugia malayi* and *Onchocerca volvulus* are responsible for most of the debilitating filarial infections in more than 80 developing countries of the tropics and sub-tropics where 1.1 billion are at risk of infection and about 150 million are infected. All three species are a source of severe pathologies that result in high morbidity and increased mortality. The infection can cause severe morbidity in up to 50% of those infected with the nematodes.

*W. bancrofti* and *B. malayi* infections can develop into lymphatic filariasis, often seen as hydrocoele in men and/or lymphedema, and in extreme cases, elephantiasis. *O. volvulus* infections can develop into severe dermatitis and/or onchocerciasis, the visual impairment giving the latter disease its common name River Blindness. Community-directed mass drug administration programs are designed to control these infections and eliminate them as a public health problem.

Current efforts aim to eliminate these parasitic nematodes through the use of drugs like diethylcarbamazine, ivermectin, and albendazole that kill the larvae, but not the adult worms. The antihelmintic drug diethylcarbamazine is used to combat lymphatic filariasis in countries without co-endemic *O. volvulus* infections, i.e., outside of Africa. Ivermectin is used to combat onchocerciasis. The greatest efficacy of both drugs is against the first stage larvae found in the blood stream or in the dermis. Since the worms can live up to 14 years and are fecund for most of their lifespan, populations in endemic regions must be treated with high coverage (at least 65%) for many years to break the transmission of the disease to uninfected persons. The presence of larvae in the skin or blood of individuals, especially children, even after many rounds of treatment additionally demonstrates that non-responders exist to the current anti-filarial drugs. There are further growing concerns that resistance in the worms may be developing. Because diethylcarbamazine can lead to severe adverse reactions in *O. volvulus* infected persons, ivermectin is effectively the sole drug available for controlling onchocerciasis.

The nematodes are host to obligate intracellular bacteria of the genus *Wolbachia*. These endobacteria are essential for embryogenesis, larval development and adult worm survival. An alternative effort aiming to eliminate the nematodes is the removal of the bacteria with antibacterial agents. While hundreds of antibiotic compounds having highly different chemical structure have been identified, it is nearly impossible to choose which compound to use in treating a specific disease.

SUMMARY

An aspect of the present invention is to provide a compound usable to treat filariasis.

In an embodiment, the present invention provides a method for a therapeutic treatment of filariasis which includes administering to a subject in need thereof an effective amount of a compound of the general formula (1)

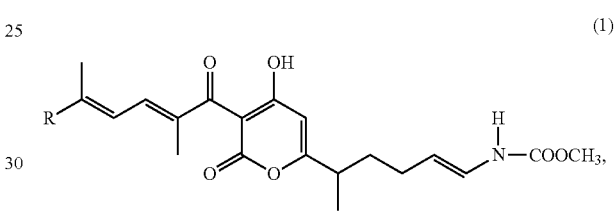

(1)

or racemates, enantiomers, diastereomers, solvates, hydrates, pharmaceutically acceptable salts, and/or esters of general formula (1), wherein, R is selected from the group comprising n-propyl, n-butyl, and structural elements (2a), (2b), (3a), (3b), (4), (5), (6a), (6b), (7a), and/or (7b):

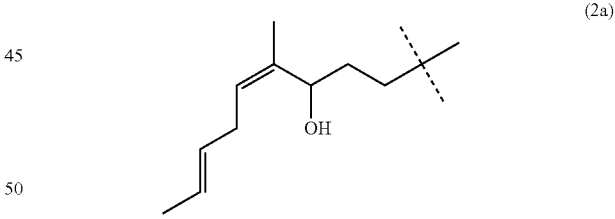

(2a)

(2b)

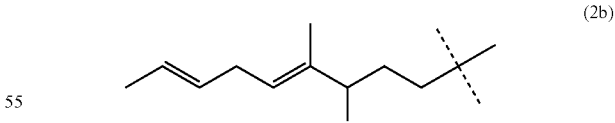

(3a)

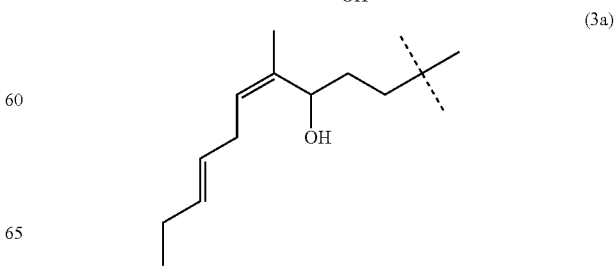

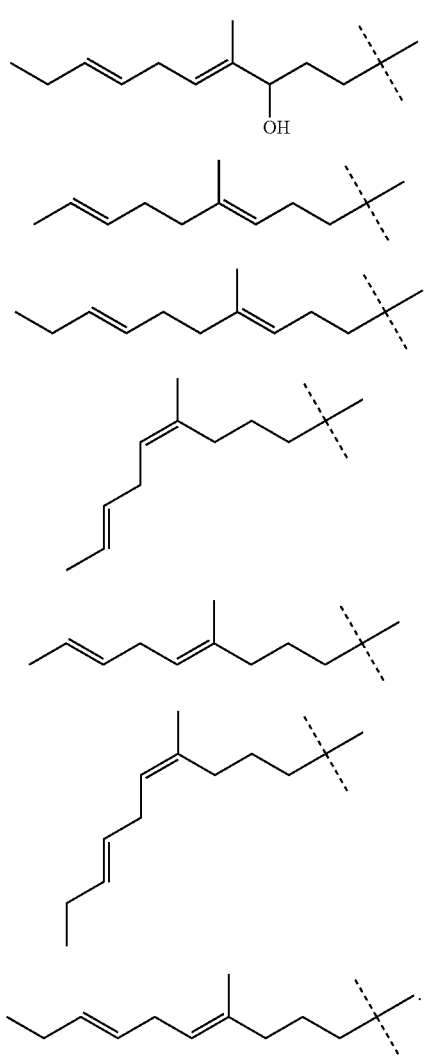

SEQUENCE LISTING

The Sequence Listing associated with this application is filed in electronic form via EFS-Web and is hereby incorporated by reference into this specification in its entirety. The name of the text file containing the Sequence Listing is Sequence_Listing_23OCT13. The size of the text file is 1,954 Bytes, and the text file was created on Oct. 23, 2013.

DETAILED DESCRIPTION

The term "filariasis" as used herein refers to helminth infections that are caused by filarial nematodes. An infection is the colonization of a host organism by parasite species. Infections with human filarial nematodes can cause lymphatic filariasis or onchocerciasis. The term "lymphatic filariasis" refers to an infection with the nematodes *Wuchereria bancrofti*, *Brugia malayi* or *Brugia timori*. The term "onchocerciasis" refers to an infection with the nematode *Onchocerca volvulus*. Lymphatic filariasis may cause hydrocoele, lymphoedema, and elephantiasis. Onchocerciasis may cause skin inflammation and blindness, so called River Blindness. In dogs, an infection with nematode species called *Dirofilaria immitis* or *Dirofilaria repens* causes dirofilariasis.

As used herein, the term "prophylactic treatment" refers to either preventing or inhibiting the development of a clinical condition or disorder or delaying the onset of a pre-clinically evident stage of a clinical condition or disorder. The term "prophylactic treatment" according to the present invention is to be understood as meaning that the compositions according to the present invention can be applied before symptoms of the infection are manifest. The term "prophylactic treatment" is to be understood as meaning a medical treatment. The compounds according to the present invention can, for example, be used in a prophylactic treatment.

The term "therapeutically effective amount" is used herein to mean an amount or dose sufficient to cause an improvement in a clinically significant condition in the subject.

Unless otherwise defined, the technical and scientific terms used herein have the same meaning as commonly understood by one of ordinary skill in the art to which the present invention belongs.

It was surprisingly found that the compounds of the present invention are effective in the treatment of filarial infections. In vitro and in vivo results demonstrated that the compounds of the present invention are effective against *Wolbachia* of filarial nematodes. The compounds of the present invention therefore have the potential to be potent anti-filarial drugs.

It is thought that the advantageous effects are derived due to the ability of the compounds of the present invention to interact with the obligate intracellular bacteria of the genus *Wolbachia* to which the nematodes are host. As the *Wolbachia* endobacteria are essential for embryogenesis, larval development and adult worm survival, the removal of the bacteria eliminates the nematodes. A treatment with the compounds of the present invention depletes the *Wolbachia* from the worms and results in blocked embryogenesis and degradation of intrauterine embryos, blocked larval development, and adult worm death.

Toxicity tests showed that treatment with the compounds of the present invention did not affect cell growth, thus indicating that the compounds did not exhibit cytotoxic effects in eukaryotes.

The compounds of the present invention have no efficacy against Gram-negative bacteria and low efficacy against *Mycobacterium* species. Mycobacteria are the causal agents of tuberculosis. The compounds of the present invention will therefore not interfere with tuberculosis treatment. The compounds of the present invention also have the potential to be used in countries endemic for filarial infections without selecting for resistant *Mycobacterium tuberculosis*.

A narrow spectrum of bacteria is moreover advantageous for the compounds of the present invention so as to reduce interference with other treatments. The compounds of the present invention thus have the potential to be used as an anti-wolbachial therapy in mass drug administration programs. Apart from that, the compounds of the present invention can be given to all members of a population.

The substituent R may be n-propyl or n-butyl. In an embodiment of the present invention, the substituent R can, for example, be n-propyl or n-butyl and the compound can, for example, be myxopyronin A or B, respectively.

In an embodiment of the present invention, the substituent R can, for example, be structural element (2a) or (3a). In an embodiment of the present invention, the substituent R can, for example, be structural element (2a) or (2b), or (3a) or (3b), and the compound can, for example, be corallopyronin A or B, respectively. Different stereoisomers of corallopyronin A and B are known. The stereoisomer (2a) of corallopyronin A can be produced by cultivation of myxobacteria naturally producing corallopyronin A.

It might be advantageous to use embodiments wherein the substituent R is n-propyl, n-butyl or is structural element (2a) or (3a) because these compounds show no toxicity towards eukaryotic cells. No cytotoxic effects were apparent in in vitro or in vivo experiments.

In an embodiment of the present invention, the compound can, for example, be the compound according to formula (8a) as indicated below and/or racemates, enantiomers, diastereomers, solvates, hydrates, and pharmaceutically acceptable salts and/or esters thereof:

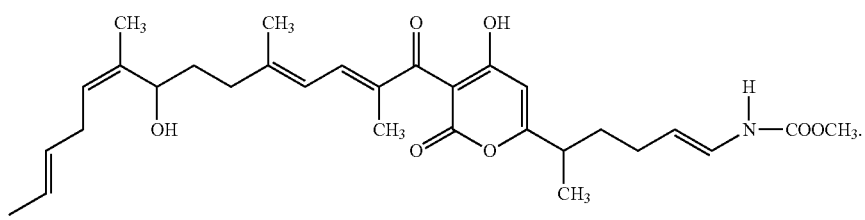

(8a)

The compounds described herein contain one or more asymmetric centers and one or more double bonds and may thus give rise to stereo or configurational isomers. The present invention includes all such possible stereo or configurational isomers as well as their mixtures, and solvates, hydrates, and pharmaceutically acceptable salts and/or esters thereof. Of the corallopyronins A and B, the myxopyronins A and B, and the pre-corallopyronins A and B, different stereoisomers are known. The present invention includes all such possible stereo or configurational isomers as well as their mixtures, and solvates, hydrates, and pharmaceutically acceptable salts and/or esters thereof.

In an embodiment of the present invention, the compound can, for example, be the compound according to formula (8b) as indicated below and/or racemates, enantiomers, diastereomers, solvates, hydrates, and pharmaceutically acceptable salts and/or esters thereof:

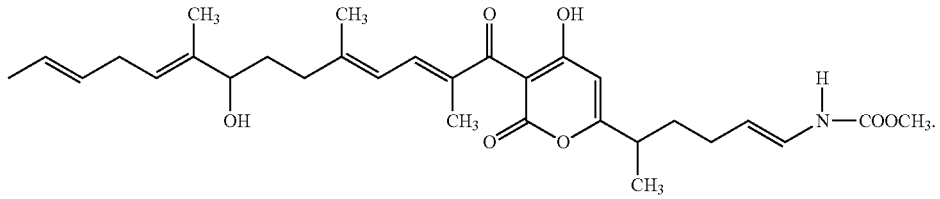

(8b)

In an embodiment of the present invention, the compound can, for example, be the compound according to formula (9a) as indicated below and/or solvates, hydrates, and pharmaceutically acceptable salts and/or esters thereof:

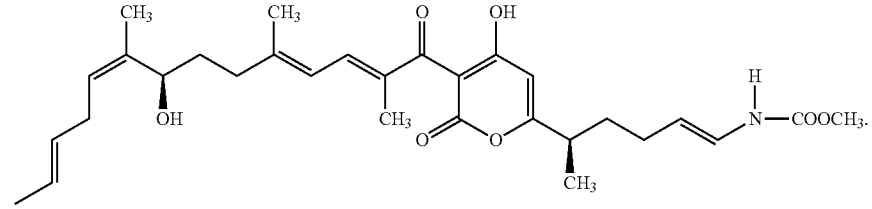

(9a)

The compound according to formula (9a) is commonly denoted corallopyronin A. Corallopyronin A also is denoted methyl N-[(1E)-5-[4-hydroxy-3-[(2E,4E,9Z,12E)-8-hydroxy-2,5,9-trimethyltetradeca-2,4,9,12-tetraenoyl]-2-oxo-2H-pyran-6-yl]hex-1-en-1-yl]carbamate according to the IUPAC nomenclature.

In an embodiment of the present invention, the compound can, for example, be the compound according to formula (9b) as indicated below and/or solvates, hydrates, and pharmaceutically acceptable salts and/or esters thereof:

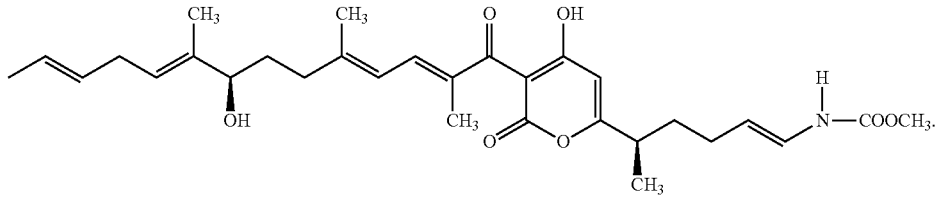

(9b)

The compound according to formula (9b) is denoted methyl N-[(1E)-5-[4-hydroxy-3-[(2E,4E,9E,12E)-8-hydroxy-2,5,9-trimethyltetradeca-2,4,9,12-tetraenoyl]-2-oxo-2H-pyran-6-yl]hex-1-en-1-yl]carbamate according to the IUPAC nomenclature.

The compound according to the formula (9a) showed a potent anti-wolbachial effect in in vitro and in vivo tests. The in vivo tests also demonstrated the expected block in nematode development resulting from the loss of their obligate intracellular *Wolbachia* bacteria. The compounds of the present invention, especially the compound according to the formula (9a), could therefore be potent anti-filarial chemotherapeutics.

The substituent R may further be structural element (4), (5), (6a) (6b), (7a) or (7b). In an embodiment of the present invention, the substituent R can, for example, be structural element (6a) or (6b), or (7a) or (7b) and the compound can, for example, be pre- corallopyronin A or B, respectively.

In an embodiment of the present invention, the compounds for use in the therapeutic or prophylactic treatment of filariasis can, for example, be selected from the group comprising corallopyronin A, corallopyronin B, pre-corallopyronins A, pre-corallopyronins B, myxopyronin A and/or myxopyronin B. In an embodiment of the present invention, the compound for use in the therapeutic or prophylactic treatment of filariasis can, for example, be corallopyronin A.

The corallopyronins and myxopyronins are synthesized by gliding myxobacteria such as *Corallococcus coralloides*. The compounds can be produced by biotechnological means, for example, cultivation of myxobacteria naturally producing the compounds, expression in myxobacterial hosts, hosts such as *Escherichia coli* (*E. coli*), actinomycetes, pseudomonads, or fungal hosts. The compounds of the present invention can alternatively be produced by chemical synthesis.

The compounds according to the present invention are further usable in the form of solvates, hydrates, and pharmaceutically acceptable salts and/or esters thereof. In an embodiment of the present invention, the compounds can, for example, be usable in the form of pharmaceutically acceptable salts thereof. The term "pharmaceutically acceptable salts" refers to salts prepared from pharmaceutically acceptable non-toxic bases or acids.

Corresponding salts of the compounds can conveniently be prepared from pharmaceutically acceptable non-toxic bases, including inorganic bases and organic bases. In an embodiment of the present invention, salts derived from inorganic bases can, for example, include ammonium, calcium, magnesium, potassium and sodium salts. Salts derived from pharmaceutically acceptable organic non-toxic bases include salts of primary, secondary, and tertiary amines, as well as cyclic amines.

In an embodiment of the present invention, the pharmaceutically acceptable salt can, for example, be selected from the group of sodium, potassium, ammonium salts, or acid addition salts. Examples of acid addition salts include hydrochloride salts or hydrochloride hydrates.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Examples include citric, hydrobromic, hydrochloric, maleic, phosphoric, sulfuric, and tartaric acids.

Pharmaceutically acceptable esters of the compounds are further usable according to the present invention. The term "pharmaceutically acceptable ester" refers to esters prepared from pharmaceutically acceptable non-toxic ester groups. In an embodiment of the present invention, the esters can, for example, be physiologically easily hydrolysable esters such as alkyl esters, for example, C1-C4 alkyl esters.

In an embodiment of the present invention, the compounds can, for example, be highly effective in depleting the endobacteria from nematodes. This allows for the administration of the compounds in low concentrations. The bioavailability of the compounds is further sufficient to reach the endobacterial target despite the many physical barriers between the body fluid and the *Wolbachia*, which are contained within intracellular vesicles. This is biologically important as antibacterial activity against an intracellular bacterium is needed. The dosage can further be kept in low concentration ranges.

The compounds can be administered during a period of ≥14 days to ≤28 days, for example, during a period of ≥10 days to ≤14 days, or, for example, during a period of ≥7 days to ≤10 days. In mice, a treatment of 28 days resulted in >99% depletion of *Wolbachia* from the nematodes.

The compounds of the present invention are highly effective in treatment of filariasis. Infections with the human filarial nematodes *Wuchereria bancrofti*, *Brugia malayi* or *Brugia timori* can cause lymphatic filariasis. Lymphatic filariasis may cause hydrocoele and lymphoedema including elephantiasis. Another filarial infection is caused by the nematode *Onchocerca volvulus*. It is the main species of filarial parasite found in the skin and tissue causing human onchocerciasis. Onchocerciasis causes skin disease and blindness. In an embodiment of the present invention, filariasis can, for example, be selected from the group comprising lymphatic filariasis and onchocerciasis. These are the main filarial infections in human. In an embodiment of the present invention, the filariasis can, for example, be dirofilariasis. Dirofilariasis refers to filarial infection in dogs.

The compounds and/or racemates, enantiomers, diastereomers, solvates, hydrates, and pharmaceutically acceptable salts and/or esters thereof can be included in a pharmaceutical composition.

Another aspect of the present invention relates to a pharmaceutical composition comprising as an active ingredient a compound according to the general formula (1) as indicated below and/or racemates, enantiomers, diastereomers, solvates, hydrates, and pharmaceutically acceptable salts and/or esters thereof:

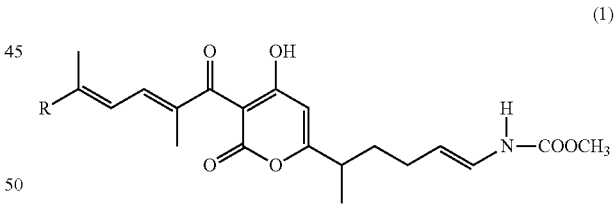

(1)

wherein,
R is selected from the group comprising n-propyl, n-butyl, and structural elements (2a), (2b), (3a), (3b), (4), (5), (6a), (6b), (7a) and/or (7b) as given as follows:

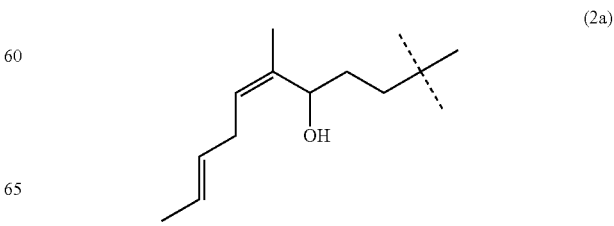

(2a)

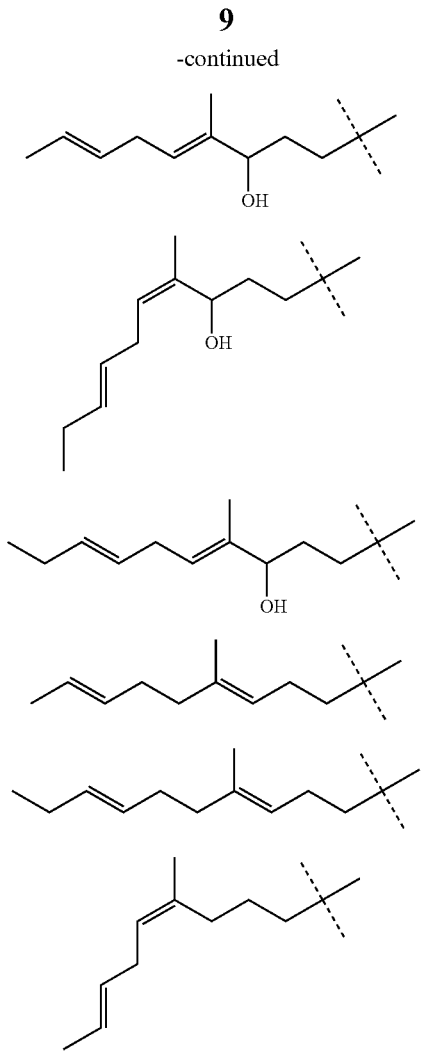

(2b)
(3a)
(3b)
(4)
(5)
(6a)

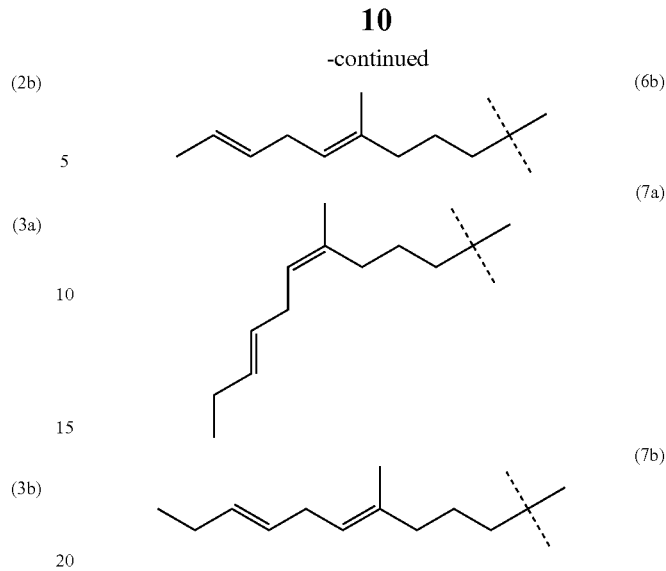

(6b)
(7a)
(7b)

for use in the therapeutic or prophylactic treatment of filariasis.

It was found that the composition comprising as an active ingredient a compound of the present invention was effective in the treatment of filarial infections.

The substituent R may be n-propyl or n-butyl. In an embodiment of the present invention, the substituent R can, for example, be n-propyl or n-butyl and the compound can, for example, be myxopyronin A or B, respectively. The substituent R can, for example, be structural element (2a) or (3a). In an embodiment of the present invention, the substituent R can, for example, be structural element (2a) or (2b), or (3a) or (3b) and the compound can, for example, be corallopyronin A or B, respectively.

In an embodiment of the present invention, the compound can, for example, be the compound according to formula (8a) as indicated below and/or racemates, enantiomers, diastereomers, solvates, hydrates, and pharmaceutically acceptable salts and/or esters thereof:

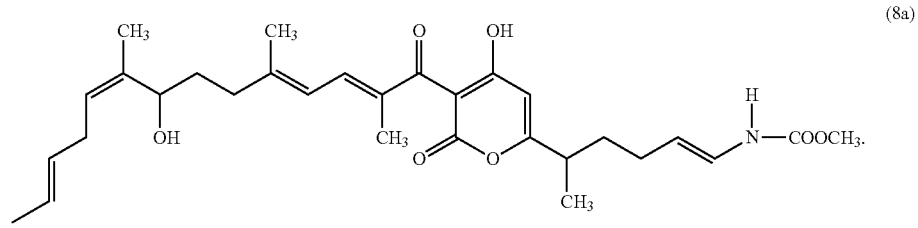 [SMILES: C/C=C/C/C=C(/C)C(O)CC/C(C)=C/C=C(\C)C(=O)c1c(O)cc(C(C)CC/C=C/NC(=O)OC)oc1=O]

(8a)

In an embodiment of the present invention, the compound can, for example, be the compound according to formula (9a) as indicated below and/or solvates, hydrates, and pharmaceutically acceptable salts and/or esters thereof:

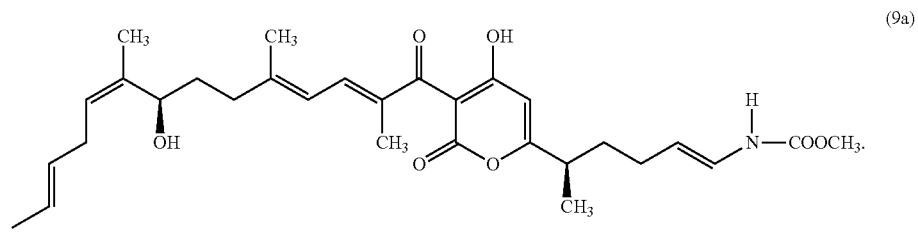 [SMILES: C/C=C/C/C=C(/C)[C@H](O)CC/C(C)=C/C=C(\C)C(=O)c1c(O)cc([C@H](C)CC/C=C/NC(=O)OC)oc1=O]

(9a)

The substituent R may further be structural element (4), (5), (6a) (6b), (7a) or (7b). In an embodiment of the present invention, the substituent R can, for example, be structural element (6a) or (6b), or (7a) or (7b) and the compound can, for example, be pre-corallopyronin A or B, respectively.

In an embodiment, the present invention relates to a pharmaceutical composition for use in the therapeutic or prophylactic treatment of filariasis comprising as an active ingredient a compound selected from the group comprising corallopyronin A, corallopyronin B, pre-corallopyronins A, pre-corallopyronins B, myxopyronin A and/or myxopyronin B. In an embodiment, the present invention relates to a pharmaceutical composition for use in the therapeutic or prophylactic treatment of filariasis comprising as an active ingredient corallopyronin A.

The compounds in the composition are further usable in form of solvates, hydrates, and pharmaceutically acceptable salts and/or esters thereof. In an embodiment of the present invention, the compounds can, for example, be usable in form of pharmaceutically acceptable salts thereof. Corresponding salts of the compounds can be conveniently prepared from pharmaceutically acceptable non-toxic bases, including inorganic bases and organic bases. Examples of salts derived from inorganic bases include ammonium, calcium, magnesium, potassium and sodium salts. Salts derived from pharmaceutically acceptable organic non-toxic bases include salts of primary, secondary, and tertiary amines, as well as cyclic amines. The pharmaceutically acceptable salt can, for example, be selected from the group of sodium, potassium or ammonium salts. The pharmaceutically acceptable salt can, for example, be acid addition salts. Examples of acid addition salts are hydrochloride salts or hydrochloride hydrates.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

Pharmaceutically acceptable esters of the compounds are further usable according to the present invention. The term "pharmaceutically acceptable ester" refers to esters prepared from pharmaceutically acceptable non-toxic ester groups. In an embodiment of the present invention, the esters can, for example, be physiologically easily hydrolysable esters such as alkyl esters, for example, C1-C4 alkyl esters.

In an embodiment of the present invention, the composition can, for example, comprise a compound according to the present invention and/or racemates, enantiomers, diastereomers, solvates, hydrates, and pharmaceutically acceptable salts and/or esters thereof as an active ingredient, a pharmaceutically acceptable carrier and optionally other therapeutic ingredients or adjuvants.

The pharmaceutical carrier can be, for example, a solid, liquid, or gas. Suitable carriers and adjuvants can be solid or liquid and correspond to the substances ordinarily employed in formulation technology for pharmaceutical formulations. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

The compositions can be suitable for oral, dermal, rectal, topical, and parenteral administration. Parenteral administration includes subcutaneous, intramuscular, and intravenous administration. The pharmaceutical compositions may be conveniently presented in unit dosage form and prepared by any of the methods well known in the art of pharmacy.

In some embodiments, the composition is formulated for oral, subcutaneous or intravenous application. In an embodiment of the present invention, the composition is formulated for oral application. Oral application provides for easy administering and dosing of the compound.

The pharmaceutical composition of the present invention can be presented as a discrete unit suitable for oral administration such as capsules, cachets or tablets each containing a predetermined amount of the active ingredient. The compositions can further be presented as a powder, as granules, as a solution, as a suspension in an aqueous liquid, as a non-aqueous liquid, as an oil-in-water emulsion or as a water-in-oil liquid emulsion. The pharmaceutical composition may further be administered by controlled release means and/or delivery devices. For compositions for oral dosage form, convenient pharmaceutical media may be employed. For example, water, glycols, oils, alcohols, flavouring agents, preservatives, colouring agents and the like may be used to form oral liquid preparations such as solutions. Carriers such as starches, sugars, microcrystalline cellulose, diluents, granulating agents, lubricants, binders, disintegrating agents, and the like may be used to form oral solid preparations such as powders, capsules and tablets. Tablets may optionally be coated by standard aqueous or non aqueous techniques.

Pharmaceutical compositions of the present invention suitable for parenteral administration may be prepared as solutions or suspensions of the active compounds in water. A suitable excipient can be included such as, for example, hydroxypropylcellulose. Dispersions can also be prepared in glycerol, liquid polyethylene glycols, and mixtures thereof in oils.

Pharmaceutical compositions of the present invention suitable for injectable use include sterile aqueous solutions or dispersions. A preservative can further be included to prevent the growth of microorganisms.

The composition of the present invention can be in a form suitable for topical use such as, for example, an aerosol, cream, ointment, lotion, dusting powder, or the like. The compositions can further be in a form suitable for use in transdermal devices. The composition may also be prepared in powder or liquid concentrate form.

The pharmaceutical composition of the present invention can include one or more additional carrier ingredients such as diluents, buffers, flavouring agents, binders, surface-active agents, thickeners, lubricants, preservatives and the like. The pharmaceutical composition may be produced under sterile conditions using standard pharmaceutical techniques well known to those skilled in the art.

A further aspect of the present invention thus relates to a pharmaceutical composition wherein the composition comprises: a) a compound according to the general formula (1) as indicated below and/or racemates, enantiomers, diastereomers, solvates, hydrates, and pharmaceutically acceptable salts and/or esters thereof:

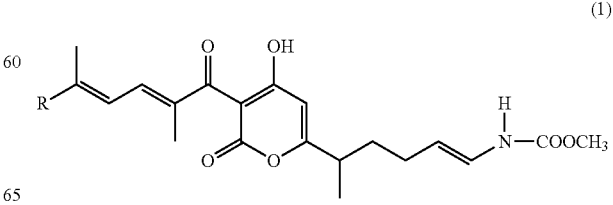

(1)

wherein,

R is selected from the group comprising n-propyl, n-butyl, and structural elements (2a), (2b), (3a), (3b), (4), (5), (6a), (6b), (7a) and/or (7b) as given as follows:

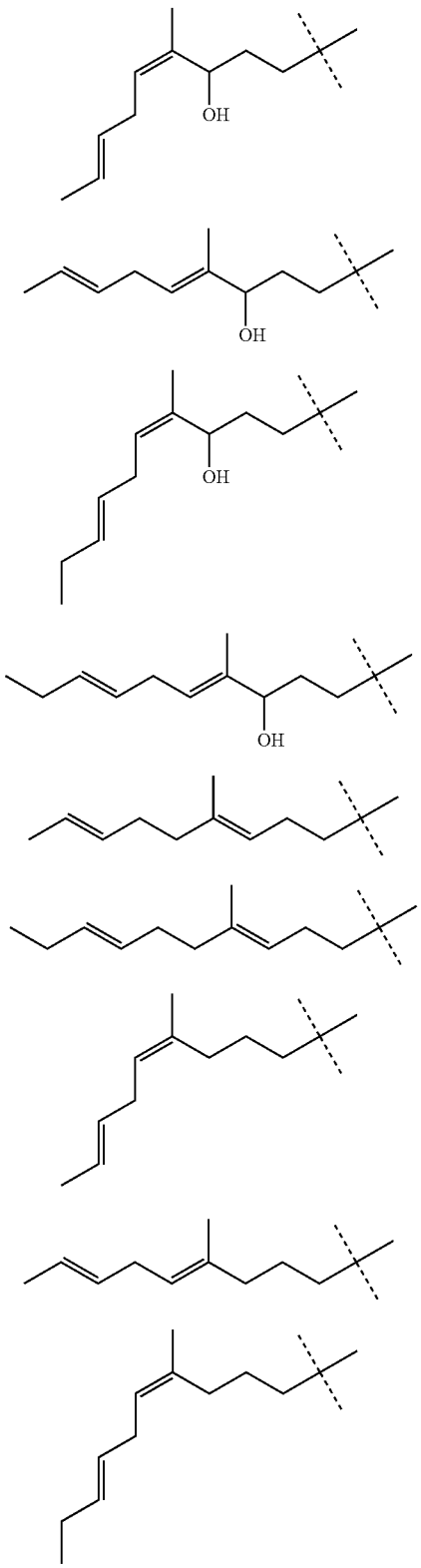

-continued

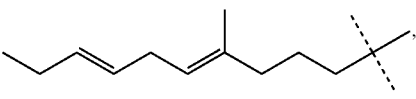
(7b)

and b) a pharmaceutically acceptable carrier for use in the therapeutic or prophylactic treatment of filariasis.

The present invention also relates to the use of a compound according to the general formula (1) as indicated below and/or racemates, enantiomers, diastereomers, solvates, hydrates, and pharmaceutically acceptable salts and/or esters thereof:

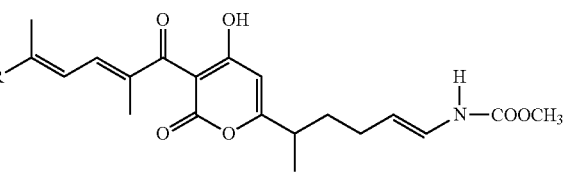
(1)

wherein,

R is selected from the group comprising n-propyl, n-butyl, and structural elements (2a), (2b), (3a), (3b), (4), (5), (6a) (6b), (7a) and/or (7b) as given as follows:

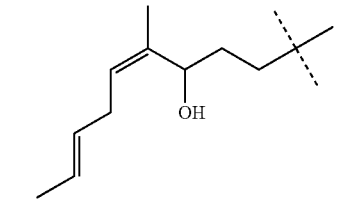
(2a)

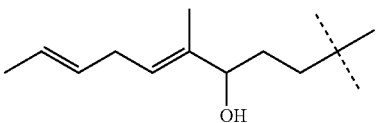
(2b)

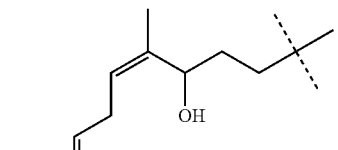
(3a)

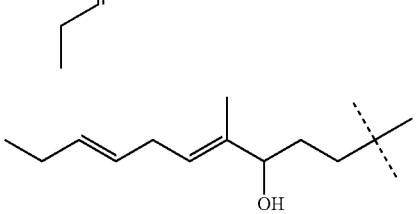
(3b)

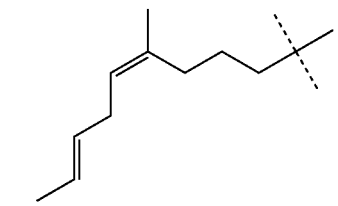
(6a)

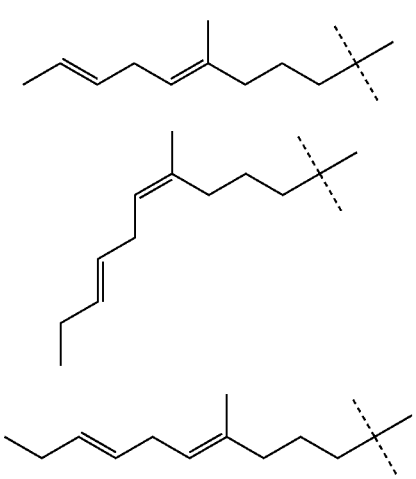

(6b)

(7a)

(7b)

for the manufacture of a medicament for the therapeutic or prophylactic treatment of filariasis.

The substituent R may be n-propyl or n-butyl. In an embodiment of the present invention, the substituent R is n-propyl or n-butyl and the compound is myxopyronin A or B, respectively. The substituent R can, for example, be structural element (2a) or (3a). In an embodiment of the present invention, the substituent R can, for example, be structural element (2a) or (2b), or (3a) or (3b) and the compound can, for example, be corallopyronin A or B, respectively.

In an embodiment of the present invention, the compound can, for example, be the compound according to formula (8a) as indicated below and/or racemates, enantiomers, diastereomers, solvates, hydrates, and pharmaceutically acceptable salts and/or esters thereof:

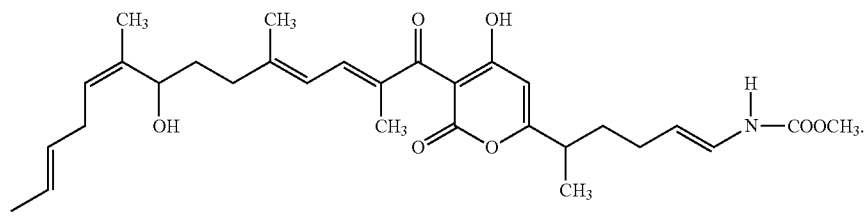
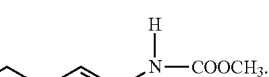

(8a)

In an embodiment of the present invention, the compound can, for example, be the compound according to formula (9a) as indicated below and/or solvates, hydrates, and pharmaceutically acceptable salts and/or esters thereof:

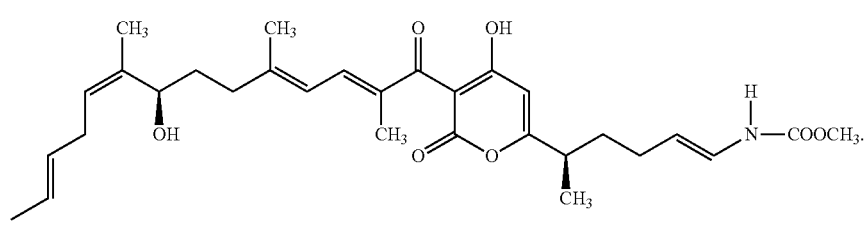
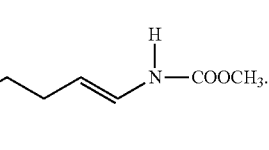

(9a)

The substituent R may further be structural element (4), (5), (6a), (6b), (7a) or (7b). In an embodiment of the present invention, the substituent R can, for example, be structural element (6a) or (6b), or (7a) or (7b) and the compound can, for example, be pre-corallopyronin A or B, respectively.

In an embodiment, the present invention relates to the use of a compound selected from the group comprising corallopyronin A, corallopyronin B, pre-corallopyronins A, pre-corallopyronins B, myxopyronin A and/or myxopyronin B for the manufacture of a medicament for the therapeutic or prophylactic treatment of filariasis. In an embodiment, the present invention relates to the use of corallopyronin A for the manufacture of a medicament for the therapeutic or prophylactic treatment of filariasis.

The compounds in the composition are further usable in form of solvates, hydrates, and pharmaceutically acceptable salts and/or esters thereof. The compounds can, for example, be usable in the form of pharmaceutically acceptable salts thereof. Corresponding salts of the compounds can conveniently be prepared from pharmaceutically acceptable non-toxic bases, including inorganic bases and organic bases. Examples of salts derived from inorganic bases include ammonium, calcium, magnesium, potassium and sodium salts. Salts derived from pharmaceutically acceptable organic non-toxic bases include salts of primary, secondary, and tertiary amines, as well as cyclic amines. The pharmaceutically acceptable salt can, for example, be selected from the group of sodium, potassium or ammonium salts. The pharmaceutically acceptable salt can, for example, be acid addition salts. Examples of acid addition salts are hydrochloride salts or hydrochloride hydrates.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. It might be advantageous to use, for example, citric, hydrobromic, hydrochloric, maleic, phosphoric, sulfuric, and tartaric acids.

Pharmaceutically acceptable esters of the compounds are further usable according to the present invention. The term "pharmaceutically acceptable ester" refers to esters prepared from pharmaceutically acceptable non-toxic ester groups. In an embodiment of the present invention, the esters are physiologically easily hydrolysable esters such as alkyl esters, for example, C1-C4 alkyl esters.

The present invention also relates to a method of treating or prophylaxing filariasis, the method comprising administering to the subject a therapeutically effective amount of a compound according to the general formula (1) as indicated below and/or racemates, enantiomers, diastereomers, solvates, hydrates, and pharmaceutically acceptable salts and/or esters thereof:

(1)
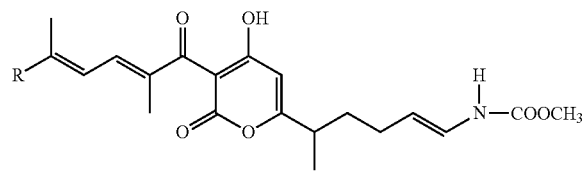

wherein,

R is selected from the group comprising n-propyl, n-butyl, and structural elements (2a), (2b), (3a), (3b), (4), (5), (6a) (6b), (7a) and/or (7b) as given as follows:

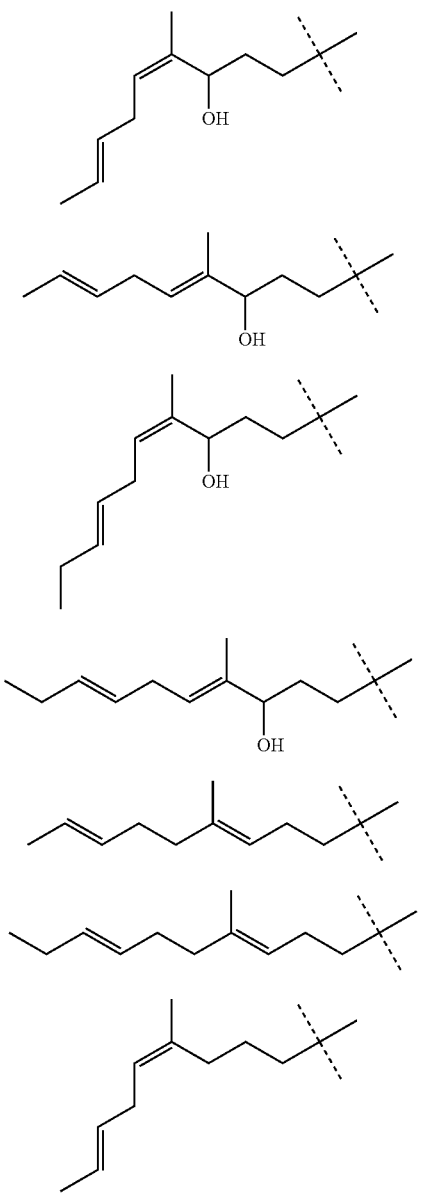

(6b)
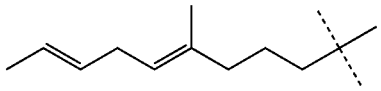

(7a)
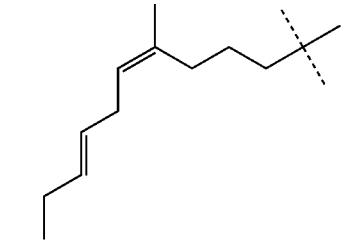

(7b)
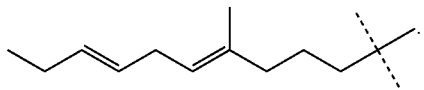

As used herein, the term "prophylaxing" refers to a "prophylactic treatment" referring to either preventing or inhibiting the development of filariasis.

In some embodiments, the method of treating or prophylaxing filariasis refers to filariasis selected from the group comprising lymphatic filariasis and onchocerciasis. In an embodiment of the present invention, the method of treating or prophylaxing filariasis refers to dirofilariasis.

In an embodiment, the present invention relates to a method of treating or prophylaxing filariasis, the method comprising administering to the subject a therapeutically effective amount of a compound selected from the group comprising corallopyronin A, corallopyronin B, pre-corallopyronins A, pre-corallopyronins B, myxopyronin A and/or myxopyronin B.

The examples which follow serve to illustrate the present invention in more detail but do not constitute a limitation thereof.

EXAMPLE 1

Cultivation and Purification of Corallopyronin A

Cultivation and purification of corallopyronin A was performed as described in Erol O. et al. "Biosynthesis of the myxobacterial antibiotic corallopyronin A", Chembiochem 11: 1253-1265, 2010 with slight modifications.

In brief, cultivation of corallopyronin A in *Corallococcus coralloides* B035 (strain collection of the Institute for Pharmaceutical Biology of the University of Bonn; the strain was isolated from a soil sample) was performed in 5 l Erlenmeyer flasks containing 1.5 l of a casitone medium (MD1 medium, supplemented with 0.2% glucose) with 2% amberlite XAD-16 (Fluka, Germany). MD1 medium comprises 3 g/l Casitone, 0.7 g/l $CaCl_2.2\ H_2O$, and 2 g/l $MgSO_4.7H_2O$. The flasks were inoculated with 200 ml of a pre-culture (grown for 4 days) of *Corallococcus coralloides* B035 cells in the same medium and shaken 140 rpm on a rotary shaker (Multitron, Infors AG, Bottmingen, Switzerland) at 30° C. for 10-14 days. At the end of the cultivation, the bacterial cells and adsorber resin were separated from the culture broth by centrifugation and extracted with acetone (6×500 ml).

After removal of the solvent by evaporation, the residue was suspended in water (250 ml) and extracted three times with ethylacetate (250 ml). The ethylacetate layers were combined and dried. Separation of this extract was done by vacuum liquid column chromatography over Polygoprep 60-50 RP (Macherey-Nagel) by consecutively employing methanol-water mixtures as eluents (gradient from 20:80 to 100:0) to get 9 fractions. ¹H-NMR spectroscopic analysis indicated that fractions 6 (70:30), 7 (80:20) and 8 (90:10) contained corallopyronin A. Theses fractions were subjected to semi-preparative RP-HPLC (column: Macherey-Nagel, Nucleodur Sphinx RP, 250×4.6 mm, 5 µm), eluent: methanol/water (70/30), flow rate: 1.5 ml/min). The fractions containing corallopyronin A were collected, combined and subsequently dried. Corallopyronin A appeared as a slightly yellow film with a mass of m/z 526 [M−H]⁻ in low-resolution electrospray ionization mass spectra (LRESIMS) measurements obtained with an Agilent 1100 system with an API 2000 Triple Quadrupole LC/MS/MS (Applied Biosystems/MDS Sciex, Foster City, Canada).

To verify that the corallopyronin A was stable over the whole period of the in vivo experiment, aliquots of the samples in phosphate buffered saline (PBS, PAA Laboratories, Cölbe, Germany) which were used for injection were analyzed by High performance liquid chromatography (HPLC). The conditions for the analytical HPLC runs were the same as above. The results showed that no degradation of corallopyronin A on days 1, 14 and 28 had occurred in comparison to the purified corallopyronin A.

EXAMPLE 2

Susceptibility of *Wolbachia* to Corallopyronin A In Vitro

The activity of corallopyronin A against *Wolbachia* was tested in vitro using the *Aedes albopictus* C6/36 cell line infected with *Wolbachia* of *A. albopictus*.

The susceptibility of *Wolbachia* towards corallopyronin A was investigated as described previously (Henrichfreise, Schiefer et al., "Functional conservation of the lipid II biosynthesis pathway in the cell wall-less bacteria *Chlamydia* and *Wolbachia*: why is lipid II needed?", (2009) Mol Microbiol, 73 (5): 913-923) with some modifications.

The *A. albopictus* cell line C6/36 (European Collection of Cell Cultures) infected with *Wolbachia* from *A. albopictus* B containing supernatant as described in Turner et al., J Immunol 2006, 177(2): 1240-1249 were cultured in 96-well plates by seeding each well with 1×10⁴ insect cells. The cells were incubated for 9 days at 26° C. in L15 Leibovitz's medium (Invitrogen, Darmstadt, Germany) supplemented with 5% fetal calf serum (FCS, Invitrogen), 1% nonessential amino acids (PAA Laboratories, Cölbe, Germany), 0.59 mg/ml tryptose phosphate broth (Sigma, Munich, Germany) and 0.01% penicillin/streptomycin (PAA Laboratories) with and without 4 µg/ml doxycycline (Merck, Darmstadt, Germany) and 1, 0.1 and 0.01 µg/ml corallopyronin A in duplicate. The medium was replaced every third day. The treated cells were harvested on day 9.

Extraction of genomic DNA was performed with the QIAamp Kit (Qiagen, Hilden, Germany) according to the instructions of the manufacturer. Depletion of *Wolbachia* was monitored by quantitative real-time PCR (qPCR) using the primers 16S-rRNA-Fw (5'-TTGCTATTAGATGAGC-CTATATTAG-3', SEQ ID NO: 1) and 16S-rRNA-Rev (5'-GTGTGGCTGATCATCCTCT-3', SEQ ID NO: 2) which target the 16S-rRNA gene (GenBank Accession #: X61767) of *Wolbachia* and Ac-Fw (5'-ACGAACTGGGAC-GATATGGA-3', SEQ ID NO: 3) and Ac-Rev (5'-GCCTCT-GTCAGGAGAACTGG-3', SEQ ID NO: 4) for actin (GenBank Accession #: DQ657949) of the C6/36 cells.

The PCR reaction mixtures were 20 µl of 1× HotStar Taq Buffer (Qiagen), 3 mM MgCl₂, 0.2 mM dNTPs (PeqLab, Erlangen, Germany), 0.5 µM forward and reverse 16S-rRNA primers or 0.3 µM forward and reverse actin primers, 0.2 µl of a 1:1000 dilution in DMSO of SybrGreen (Roche, Mannheim, Germany), 0.5 units HotStar Taq polymerase and 2 µl of gDNA. The real-time PCR was performed in a Rotor Gene 3000 (Corbett Life Science, Sydney, Australia) using the following conditions: 95° C. for 15 minutes followed by 45 cycles of 10 seconds 95° C., 15 seconds 55° C. (16S-rRNA) or 57° C. (actin), and 20 seconds 72° C. with fluorescent signal acquired on the FAM channel (470 nm excitation, 510 nm detection). Specific amplification was confirmed by a melting curve analysis from 72° C. to 95° C. with fluorescence acquired on the FAM channel at 1° C. intervals. The copy number of each gene was calculated using a plasmid containing the appropriate insert as standard curve. To normalize the loss of *Wolbachia*, the 16S-rRNA copy number was divided by the actin copy number to generate the 16S-rRNA/actin ratio.

It could be seen that after nine days of treatment, corallopyronin A had depleted the *Wolbachia* from the C6/36 cell line. Corallopyronin A depleted >50% of the *Wolbachia* beginning at 0.1 µg/ml and had at 1 µg/ml depleted *Wolbachia* to levels equivalent to 4 µg/ml of the tetracycline doxycycline. To control for possible toxicity to the C6/36 cells, the actin copy numbers were compared. All treatments that depleted *Wolbachia* did not affect cell growth at the concentrations tested.

It could be demonstrated that in the nine day assay, corallopyronin A depleted *Wolbachia* in a dose dependent manner. Moreover, at 1 µg/ml, Corallopyronin A depleted the endobacteria from the cells to levels equivalent to those of 4 µg/ml doxycycline. Corallopyronin A thus proved to be a highly effective anti-wolbachial treatment.

Corallopyronin A further had anti-wolbachial activity also without apparent cytotoxic effects.

EXAMPLE 3

Susceptibility of *Wolbachia* to Corallopyronin A In Vivo

The effect of corallopyronin A in vivo was determined in a rodent model of BALB/c mice infected with the rodent filarial worm *Litomosoides sigmodontis* host to *Wolbachia*. *L. sigmodontis* is a well established model for human filarial worms. A key advantage of this model is the fact that administration of anti-wolbachial drugs concomitant with infection by the *L. sigmodontis* larvae allows for a rapid assessment of activity on the day the worms are retrieved from the infected animals. If the therapy is an effective anti-wolbachial, larval development will be blocked and the worms from treated animals will be significantly shorter in length, a phenotype that is visible to the naked eye.

The *L. sigmodontis* life cycle was maintained at the Institute for Medical Microbiology, Immunology and Parasitology as described by Al-Qaoud K M et al. (1997) "Infection of BALB/c mice with the filarial nematode *Litomosoides sigmodontis*: role of CD4+ T cells in controlling larval development", Infect Immun 65: 2457-2461.

Female BALB/c mice aged 6-8 weeks were purchased from Charles River, Sulzfeld, Germany. The mice were infected with *L. sigmodontis* larvae as described in by Al-Qaoud K M et al. Beginning the day after the infection, the mice were untreated or given intra-peritoneal injections of: 10% dimethyl sulfoxide (DMSO) (vehicle control), 50 mg/kg/day doxycycline (Merck), or 35 mg/kg/day of corallopyronin A. Doxycycline was given for 14 days while corallopyronin A and 10% DMSO (vehicle control) were given for 28 days. All substances were diluted in phosphate buffered saline (PBS, PAA Laboratories).

To control for degradation over time, an aliquot of corallopyronin A was frozen for HPLC analysis on days 1, 14 and 28. Five weeks post infection worms were recovered from the pleural cavity by lavage with PBS. The worms were sorted by sex with the aid of a dissecting microscope and their lengths measured. 10 female worms from each treatment were individually frozen for DNA extraction.

Genomic DNA was extracted from individual worms using the reagents from a QIAamp mini kit (Qiagen). The Qiagen protocol with the following changes was used: the worms were incubated with proteinase K overnight at 56° C.; Wizard SV96 DNA binding plates (Promega, Mannheim, Germany) and vacuum manifold instead of DNA columns were used to bind, wash and elute the DNA in 50 µl of 10 mM Tris, 0.5 mM EDTA, pH 9. Elution plates were sealed with plastic and kept at −20° C. until used for qPCR.

Depletion of *Wolbachia* was monitored by qPCR using the primers Ls-FtsZ-Fw (5'-CGATGAGATTATGGAA-CATATAA-3', SEQ ID NO: 5) and Ls-FtsZ-Rev (5'-TTG-CAATTACTGGTGCTGC-3', SEQ ID NO: 6) and hybridization probe (5'-6-FAM-CAGGGATGGGTGGTGGTACTGGAA-TAMRA-3', SEQ ID NO: 7) which target ftsZ (GenBank Accession #: AJ010271), a single copy number gene of *Wolbachia*. The PCR mixture was a 10 µl volume of 1× HotStar Taq Buffer (Qiagen), 4.5 mM $MgCl_2$, 0.2 mM dNTPs (PeqLab), 0.05 µM hybridization probe, 0.3 µM of each primer, 0.25 units of HotStar Taq Polymerase and 2 µl gDNA. Cycling conditions were: 95° C. for 15 minutes followed by 35 cycles of 94° C. for 4 seconds, 58° C. for 30 seconds and 72° C. for 15 seconds with fluorescence acquired on the FAM channel as described in Arumugam S et al., Int J Parasitol 2008, 38: 981-987.

To normalize the ftsZ content of worms of different lengths, the *L. sigmodontis* actin gene (GenBank Accession No.: GU971367) was quantified by qPCR using the primers Ac-Fw (5'-GTGCTACGTTGCTTTGGACT-3', SEQ ID NO: 8) and Ac-Rev (5'-GTAATCACTTGGCCATCAGG-3', SEQ ID NO: 9). The PCR reaction mixture was 10 µl of 1× HotStar Taq Buffer (Qiagen), 3.5 mM $MgCl_2$, 0.2 mM dNTPs (PeqLab), 0.9 µM forward and reverse actin primers, 0.1 µl of a 1:1000 dilution in DMSO of SybrGreen (Roche), 0.25 units HotStar Taq polymerase and 2 µl of gDNA. The real-time PCR was performed in a Rotor Gene 3000 (Corbett Life Science) using the following conditions: 95° C. for 15 minutes followed by 35 cycles of 10 seconds 95° C., 20 seconds 57° C., and 20 seconds 72° C. with fluorescent signal acquired on the FAM channel. Specific amplification was confirmed by a melting curve analysis as above. The copy number of each gene was calculated using a plasmid containing the appropriate insert as standard curve as described in Strubing U et al. Int J Parasitol 2010, 40: 1193-1202.

Normal distribution of the data was calculated using the D'Agostino & Pearson omnibus normality test. For comparing the level of *Wolbachia* depletion in worms, the Kruskal-Wallis test with Dunn's Multiple Comparison Test was performed. For comparing *Wolbachia* depletion from the C6/36 cells and worm length between the treatment groups, the One-way ANOVA with Bonferroni's Multiple Comparison Test was performed. Alls statistics were calculated using GraphPad Prism version 5.00 for Windows, GraphPad Software, San Diego Calif. USA, www.graphpad.com.

It could be seen that treating the infected BALB/c mice for 28 days with 35 mg/kg/day Corallopyronin A resulted in the depletion of >99% of the *Wolbachia* compared to the control. The vehicle control had no effect on the *Wolbachia* content of the worms.

As a result of the *Wolbachia* depletion by doxycycline treatment for 14 days the worms were significantly shorter (median 8.3 mm) compared to the untreated (38 mm) or vehicle controls (34 mm). Corallopyronin A given for 28 days at 35 mg/kg/day also resulted in significantly shorter worms compared to the control worms (9.0 mm versus 38 mm, respectively), again indicating that this dosage regime was equivalent to the shorter treatment time with a higher dose of doxycycline. Corallopyronin A was further able to transit the many barriers of worm cortical, host cell membrane, vesicle membranes, and endobacterial membrane that separate the endobacteria from the pleural cavity, where the larvae are located in the mice.

Using the *L. sigmodontis* model, it was seen that *Wolbachia* were depleted from the worms to levels below those seen for doxycycline at 50 mg/kg/day for 14 days when administered at 35 mg/kg/day for 28 days.

Corallopyronin A treatment of infected mice concomitant with the infection also resulted in significantly shorter worms. Corallopyronin A was well tolerated by the mice at the 35 mg/kg/day dosage used and no toxic effects were visually apparent.

The in vivo results further confirmed that the bioavailability of the compounds in the mouse is sufficient to reach the endobacterial target despite the many physical barriers between the fluid of the pleural cavity which is the site of *L. sigmodontis* adult worms and the *Wolbachia*, which are contained within intracellular vesicles. The latter point is biologically important as the in vivo results have demonstrated antibacterial activity of corallopyronin A against an intracellular bacterium.

The present invention is not limited to embodiments described herein; reference should be had to the appended claims.

What is claimed is:

1. A method for treating filariasis, the method comprising administering to a subject in need thereof an effective amount of a compound of the general formula (1)

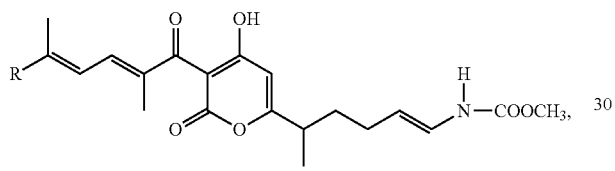
(1)

or at least one of racemates, enantiomers, diastereomers, solvates, hydrates, pharmaceutically acceptable salts, and esters of general formula (1), wherein, R is selected from the group comprising n-propyl, n-butyl, and at least one of structural elements (2a), (2b), (3a), (3b), (4), (5), (6a), (6b), (7a), and (7b):

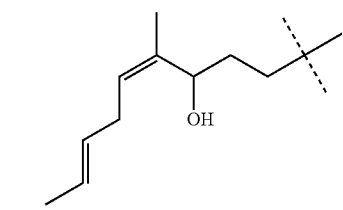
(2a)

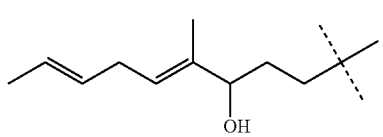
(2b)

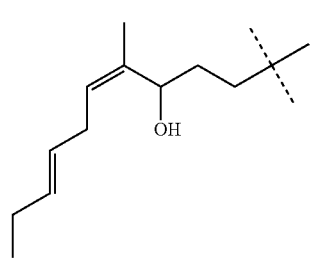
(3a)

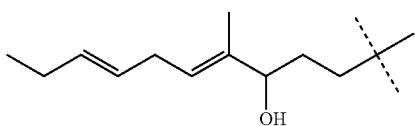
(3b)

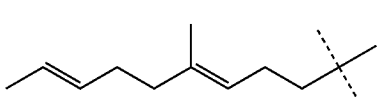
(4)

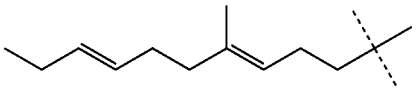
(5)

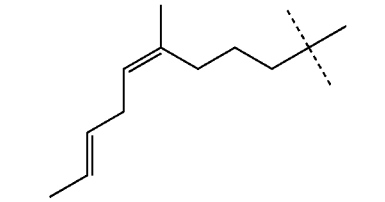
(6a)

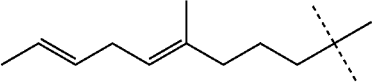
(6b)

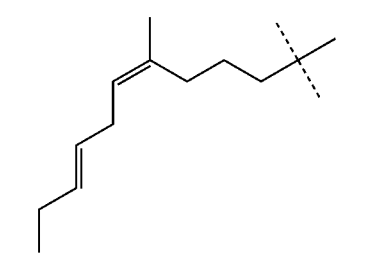
(7a)

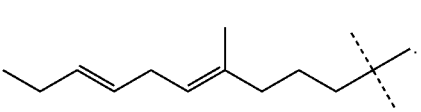
(7b)

2. The method as recited in claim 1, wherein the compound is the compound of formula (8a):

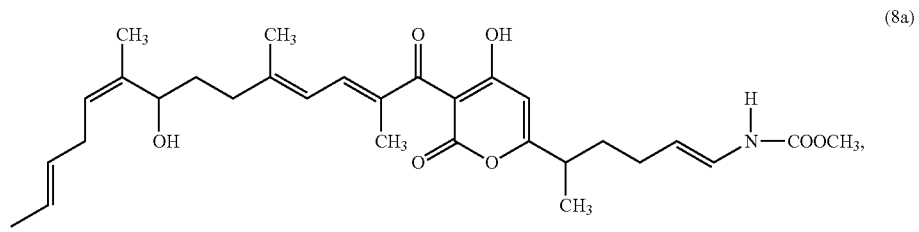 [SMILES: C/C=C/C/C=C(/C)C(O)CC/C(C)=C/C=C(\C)C(=O)c1c(O)cc(C(C)CC/C=C/NC(=O)OC)oc1=O]

(8a)

or at least one of racemates, enantiomers, diastereomers, solvates, hydrates, pharmaceutically acceptable salts, and esters of the formula (8a).

3. The method as recited in claim 1, wherein the compound is the compound of formula (9a)

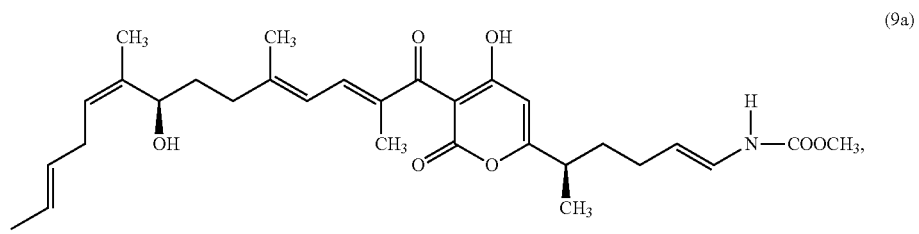 [SMILES: C/C=C/C/C=C(/C)[C@H](O)CC/C(C)=C/C=C(\C)C(=O)c1c(O)cc([C@H](C)CC/C=C/NC(=O)OC)oc1=O]

(9a)

or at least one of solvates, hydrates, pharmaceutically acceptable salts, and esters of formula (9a).

4. The method as recited in claim 1, wherein R is structural element (6a)

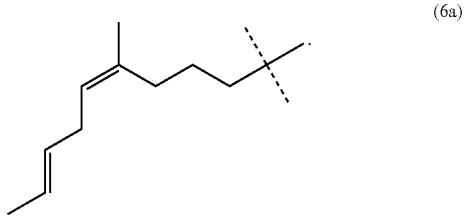

(6a)

5. The method as recited in claim 1, wherein the filariasis is selected from the group comprising lymphatic filariasis and onchocerciasis.

6. The method as recited in claim 1, wherein the filariasis is dirofilariasis.

7. The method as recited in claim 1, wherein the subject is a human.

8. The method as recited in claim 1, wherein the subject is an animal.

9. The method as recited in claim 1, wherein the subject is a dog.

10. The method as recited in claim 1, wherein the subject is a dog and the filariasis is dirofilariasis.

11. The method as recited in claim 1, wherein the subject is an animal and the filariasis is dirofilariasis.

12. The method as recited in claim 1, wherein the subject is a human and the filariasis is at least one of lymphatic filariasis and onchocerciasis.

* * * * *

SEQUENCE LISTING

<160> NUMBER OF SEQ ID NOS: 9

<210> SEQ ID NO 1
<211> LENGTH: 25
<212> TYPE: DNA
<213> ORGANISM: Artificial
<220> FEATURE:
<223> OTHER INFORMATION: primer

<400> SEQUENCE: 1
ttgctattag atgagcctat attag                                    25

<210> SEQ ID NO 2
<211> LENGTH: 19
<212> TYPE: DNA
<213> ORGANISM: Artificial
<220> FEATURE:
<223> OTHER INFORMATION: primer

<400> SEQUENCE: 2
gtgtggctga tcatcctct                                           19

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
acgaactggg acgatatgga                                          20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
gcctctgtca ggagaactgg                                          20

<210> SEQ ID NO 5
<211> LENGTH: 23
<212> TYPE: DNA
<213> ORGANISM: Artificial
<220> FEATURE:
<223> OTHER INFORMATION: primer

<400> SEQUENCE: 5
cgatgagatt atggaacata taa                                      23

<210> SEQ ID NO 6
<211> LENGTH: 19
<212> TYPE: DNA
<213> ORGANISM: Artificial
<220> FEATURE:
<223> OTHER INFORMATION: primer

<400> SEQUENCE: 6
ttgcaattac tggtgctgc                                           19

<210> SEQ ID NO 7
<211> LENGTH: 24
<212> TYPE: DNA
<213> ORGANISM: Artificial
<220> FEATURE:
<223> OTHER INFORMATION: hybridization probe

<400> SEQUENCE: 7
cagggatggg tggtggtact ggaa                                     24

<210> SEQ ID NO 8
<211> LENGTH: 20
<212> TYPE: DNA

```
<213> ORGANISM: Artificial
<220> FEATURE:
<223> OTHER INFORMATION: primer

<400> SEQUENCE: 8
gtgctacgtt gctttggact                                              20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
gtaatcactt ggccatcagg                                              20
```